United States Patent [19]

Francalanci et al.

[11] Patent Number: 5,248,601
[45] Date of Patent: Sep. 28, 1993

[54] PROCESS FOR PREPARING L(−)-CARNITINE CHLORIDE

[76] Inventors: Franco Francalanci, 7 Via G. Ferraris; Marco Ricci, 5, Via Brescia, both of 28100 Novara; Pietro Cesti, 51, Via Torino, 28069 Trecate, Novara; Carlo Venturello, 135, Via XXIII Marzo, 28100 Novara, all of Italy

[21] Appl. No.: 595,670

[22] Filed: Oct. 9, 1990

Related U.S. Application Data

[63] Continuation of Ser. No. 25,675, Mar. 13, 1987, abandoned.

[30] Foreign Application Priority Data

Mar. 14, 1986 [IT] Italy .............................. 19762 A/86

[51] Int. Cl.$^5$ ...................... C12P 13/00; C12P 15/00; C12P 7/62; C12P 7/00
[52] U.S. Cl. .................................. 435/128; 435/127; 435/132; 435/135; 435/280; 435/123; 435/252.1
[58] Field of Search ............... 435/127, 128, 132, 135, 435/280, 123, 252.1

[56] References Cited

U.S. PATENT DOCUMENTS

| | | | |
|---|---|---|---|
| 4,371,618 | 2/1983 | Cavazza | 435/128 |
| 4,642,290 | 2/1987 | Sih | 435/128 |
| 4,732,853 | 3/1988 | Whitesides et al. | 435/123 |

FOREIGN PATENT DOCUMENTS

| | | |
|---|---|---|
| 60595 | 9/1982 | European Pat. Off. |
| 122794 | 10/1984 | European Pat. Off. |
| 141408 | 5/1985 | European Pat. Off. |
| 094295 | 11/1982 | Japan |
| 1075563 | 7/1967 | United Kingdom |
| 2131049 | 6/1984 | United Kingdom |

OTHER PUBLICATIONS

Fritz et al., Carnitine Acetyltransferase, Biological Chemistry, vol. 249, No. 5, pp. 2188-2192 (May 1965).
Row et al., L-Carnitine Therapy in Propionicacidaemia, Lancet, Jun. 19, 1982, pp. 1411-1412.
Barel et al., "Comparative Studies of the Enzymatic Properties of Novo and Carlsberg Subtilisins", *J of Biol. Chem.*, vol. 243, No. 7 Apr. 10 pp. 1344-1348 1968.
Joues et al. "Techniques of Chemistry", vol. X, (ed), Part 1, 1976, Wiley, pp. 137-167.

*Primary Examiner*—Irene Marx
*Attorney, Agent, or Firm*—Byan Cave

[57] ABSTRACT

A biotechnological process for preparing L(−)-carnitine chloride, having the formula $$CH_3-\overset{\overset{\displaystyle CH_3}{|}}{\underset{\underset{\displaystyle CH_3}{|}}{N^+}}\underset{}{\overset{OH}{\diagdown}}\underset{}{\overset{H}{\diagup}}COOH \; Cl^- \quad (I)$$

comprising:
(a) reacting a racemic ester of (R,S)-3,4-epoxybutyric acid having the formula $$CH_2\!\!-\!\!CH\!\!-\!\!CH_2\!\!-\!\!COOR \quad (II)$$
$$\diagdown\!\!O\!\!\diagup$$

wherein R is an alkyl group having from 1 to 10 carbons or a benzyl group, with an enzyme capable of selectively hydrolyzing enantiomer S(−);
(b) separating the enantiomer S(−) from non-reacted ester which is present in predominantly the R(+) form;
(c) reacting the non-reacted ester obtained in step (b) with an enzyme capable of quantitatively hydrolyzing the R(+) form to obtain thereby a salt of 3,4-epoxybutyric acid in the R(+) form having the formula $$CH_2\!\!-\!\!CH\!\!-\!\!CH_2\!\!-\!\!COO^-X^+ \quad (III)$$
$$\diagdown\!\!O\!\!\diagup$$

wherein X is Na, K, or Li;
(d) reacting the salt obtained in step (c) with a molar excess of trimethylamine; and
(e) treating the reaction product of step (d) with HCl to remove excess trimethylamine and to obtain thereby the L(−)-carnitine chloride of formula (I).

15 Claims, No Drawings

PROCESS FOR PREPARING L(−)-CARNITINE CHLORIDE

This is a continuation of U.S. application Ser. No. 025,675 filed Mar. 13, 1987 (abandoned).

TECHNICAL FIELD

The present invention relates to a biotechnological process for preparing L(−)-carnitine chloride having the formula:

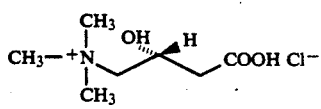

More particularly, the present invention relates to a process for preparing L(−)-carnitine chloride by reacting trimethylamine with an alkaline salt of R(+)-3,4-epoxybutyric acid. The alkaline salt of R(+)-3,4-epoxybutyric acid is obtainable from two successive enzymatic hydrolysis reactions of certain esters of the racemic 3,4-epoxybutyric acid.

BACKGROUND OF THE INVENTION

It is known that carnitine (also known as β-hydroxy-γ-trimethylaminobutyric acid) has a center of asymmetry in the β position and, therefore, two stereoisomers may exist. The stereoisomers are referred to as the D and L forms, antipodes, or optical enantiomers.

L(−)-carnitine chloride has an important role in human metabolism, particularly in the transfer of fatty acids. D(+)-carnitine, on the other hand, is an inhibiting agent which competes with L(−)-carnitine for the enzyme L(−)-carnintineacyltransferase, possibly resulting in lowering the level of L(−)-carnitine present in cardiac tissue. Fritz, I. B., Schultz, S. K, J. Biol. Chem. (1965) 240 2188; Roe, C. R., Bohan, T. P., Lancet (1982) 1411.

The commonly known therapeutic uses of L(−)-carnitine are as an eutrophyic agent and as a cardioprotecting agent in the treatment of myocardial ischemias, angina pectoris and schlerois of the myocardium.

There are processes known for synthesizing carnitine. Most of the known processes, however, result in the production of carnitine in both the D and L forms. Thus, an additional step is required for separating the racemic mixture into its two optical enantiomers. These known processes require expensive reactants which are optically active such as, for example, dibenzoyltartaric acid, camphoric acid, mandelic acid, and the like. Additionally, the reaction conditions must be carefully controlled. Also, several crystallization steps are necessary. Consequently, known processes for synthesizing L(−)-carnitine are generally economically burdensome and thus impractical for industrial application. (See European Patent Application EP 141,408; French Patent 1,466,696 and British Patent G.B. - A - 2,131,049.)

There is also described a process for synthesizing L(−)-carnitine from an optically active compound such as D-mannitol (see European Patent Application EP 60,595). While this process does not require separation of D and L enantiomers, the synthesis is complex in that a large number of individual steps must be performed. Moreover, expensive and potentially dangerous reactants such as lead tetraacetate are used in the process.

Some microbiological processes for preparing L(−)-carnitine from prochiralic substrates, such as alkyl chloroacetoacetates, crotonobetaines or butyrobetaines are also known (see Belgian Patent BE 898,396; European Patent Application EP 122,794; French Patent Application FR 2,485,564). Such processes have the disadvantages of requiring bulky reaction volumes, resulting in low yields, and difficulty in purifying the products.

Therefore, there is a need for a simple, efficient and economical process for preparing L(−)-carnitine on an industrial scale.

The present invention provides a method for the preparation of L(−)-carnitine chloride which is simple to perform and advantageous from an industrial standpoint.

SUMMARY OF THE INVENTION

It has now been found that L(−)-carnitine may be prepared by a biotechnological process comprising reacting trimethylamine with an alkaline salt of R(+)-3,4-epoxybutyric acid, the latter being obtained by two successive enzymatic hydrolyzations of esters of racemic 3,4-epoxybutyric acid. The trimethylamine reaction product is treated with HCl, to thereby obtain L(−)-carnitine chloride.

The enzymatic hydrolysis of the esters of (R,S)-3,4-epoxy-butyric acid requires two different enzymes, which are capable of hydrolyzing, respectively:

(a) the enantiomer S(−) of the racemic ester, selectively, and (b) the enantiomer R(+) of the ester.

DETAILED DESCRIPTION OF THE INVENTION

The present invention provides a process for the biotechnological synthesis of L(−)-carnitine chloride having the formula .

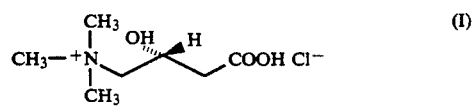

comprising the steps of (a) reacting a racemic ester (R,S)-3,4-epoxybutyric acid having the formula

wherein R is an alkyl group having from 1 to 10 carbons, or a benzyl group, with an enzyme capable of selectively hydrolyzing enantiomer S(−), asymmetrically, the hydrolysis being carried out under controlled pH conditions;

(b) separating the hydrolyzed enantiomer S(−) from non-reacted ester, present as predominantly the R(+) enantiomer;

(c) reacting the non-reacted R(+) enantiomer obtained in step (b) with an enzyme capable of quantitatively hydrolyzing the R(+) enantiomer under controlled pH conditions to obtain a salt of 3,4-epoxybutyric acid, predominantly as the R(+) form, having the formula

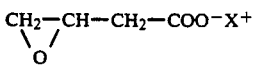

wherein X is Na, K, or Li;

(d) reacting the R(+) salt of 3,4-epoxybutyric acid obtained in step (c) with a molar excess of trimethylamine; and (e) removing the excess of trimethylamine with hydrochloric acid to obtain thereby the L(−)-carnitine chloride of formula I.

In another embodiment of the process of the invention, hydrolysis of the racemic ester of (R,S)-3,4-epoxybutyric acid may be carried out in the presence of a microorganism capable of producing an enzyme for selectively hydrolyzing, asymmetrically, the enantiomer S(−).

The racemic esters of formula (II) are known compounds and may be prepared according to known methods, for example:

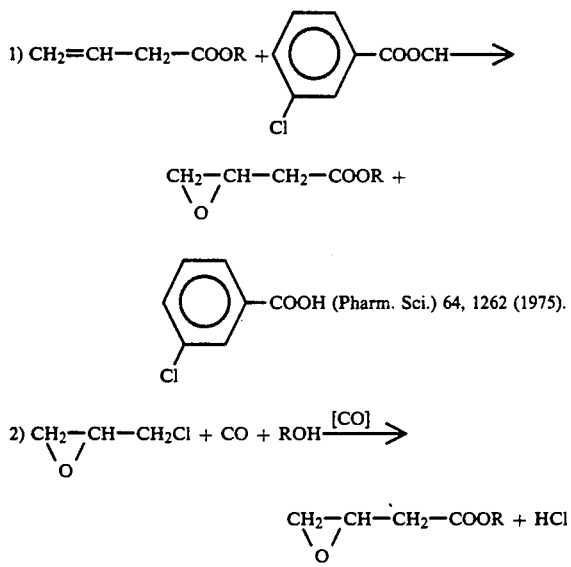

As previously discussed, the racemic esters of formula (II) are reacted with enzymes capable of hydrolyzing substantially only the (S)- enantiomer. Useful enzymes may be obtained from microorganisms or may be of animal origin, provided that the enzyme is capable of selectively hydrolyzing enantiomer S(−), leaving the enantiomer R(+) substantially unaltered (asymmetric hydrolysis).

Known enzymes have been found useful for this purpose. Examples of suitable enzymes which have been found to be particularly effective are:

| Enzyme | Origin | Producer |
|---|---|---|
| Steapsin | swine pancreas | SIGMA Chem. Co. St. Louis - USA |
| Pancreatin | swine pancreas | UNIBIOS - Trecate (Italy) |
| Lipase from Candida cylindracea superscript 1 | Candida cylindracea | SIGMA Chem. Co. St. Louis - USA |
| Esterase from swine liver | swine liver | SIGMA Chem. Co. St. Louis - USA |

1. commonly known as Candida rugosa

It should be understood, however, that other enzymes capable of the required selective hydrolysis as are known to those skilled in the art are also useful.

As previously discussed, the hydrolysis of the racemic ester may also be carried out in the presence of microorganisms producing appropriate hydrolytic enzymes. Thus, any microorganism which produces enzymes capable of hydrolyzing, asymmetrically, the racemic esters having formula (II) are useful.

The following microorganisms have been found to be particularly effective:

| | | |
|---|---|---|
| Pseudomonas fragi | IFO | 3458 |
| Bacillus subtilis | ATCC | 6633 |
| Rodotorula minuta | IFO | 0879 |
| Candida cylindracea | ATCC | 14830 |
| Arthrobacter simplex | IFO | 3530. |

The listed microorganisms have been deposited with depositories under the accession numbers shown in the right-most column, above. The American Type Culture Collection (ATCC) is located at:

12301 Parklawn Drive
Rockville, Md. 20852

The Institute for Fermentation Osaka (IFO) is located at:

17-85 Yuso-Honmachi-2-Chome
Yodogawa-ku
Osaka 532, Japan.

In carrying out the method of the invention, the asymmetric hydrolysis of the racemic esters of formula (II) [step (a)] is carried out under vigorous stirring of a mixture comprising ester and enyzme. Typically, the enzyme is present in an amount ranging from between 0.03–10% by weight of the racemic ester. The concentration of the racemic ester is generally from between 1 to 20% by weight of the reaction mixture. In a preferred embodiment, an aqueous solution of a raw or purified enzyme is used. Alternatively, the enzyme may be immobilized on suitable substrates as are known to those skilled in the art.

In another embodiment, the racemic ester is mixed with a broth containing a microorganism capable of elaborating the required enzyme, or a filtrate, concentrate or suspension of the microorganism, as the source of the hydrolyzing enzyme.

The hydrolysis of step (a) is carried out at a temperature from about 5° C. to 60° C., preferably from about 10° C. to 30° C.

The pH of the reaction mixture is maintained from about 5 to 9, and preferably from between 6 to 8. It is believed that the enzymes are most active in a pH range of from about 5 to 9. The pH of the reaction mixture is controlled with a buffer, preferably a Na or K buffer solution. Another method of controlling the pH of the reaction mixture is by neutralizing the acids formed during the reaction with a mineral base such as, for example, NaOH, KOH, LiOH, CaCO$_3$, and the like.

Typically, the asymmetric hydrolysis of the racemic ester (step (a)) proceeds for a period of from about 5 to 72 hours, depending on the specific activity of the enzyme used, or the amount of conversion desired.

When the asymmetric hydrolysis reaction is complete, the non-reacted ester (formula II), rich in enantiomer R(+), is separated from the reaction mixture. Preferably, the R(+) enantiomer is extracted by using a solvent immiscible with water. Suitable solvents include methylene chloride, toluene, ligroine, ethyl ether, etc. The extracted R(+) enantiomer is then purified according to known techniques such as, for example, distillation or column chromatography.

The R(+) enantiomer of the ester (formula (II)), is generally not easily hydrolyzed by means of standard chemical methods because of the high reactivity of the oxyranic ring under the reaction conditions. In accordance with the present invention, it has been found that the R(+) enantiomer of the ester (formula II) is easily hydrolyzed by selected hydrolytic enzymes capable of quantitatively hydrolyzing ester R(+) (formula II) to form a salt of 3,4-epoxybutyric acid, substantially all in the R(+) form. Commercially available hydrolytic enzymes are useful for carrying out the hydrolysis reaction of step (c).

Among suitable hydrolytic enzymes, the following enzymes have been found to be particularly effective.

| Enzyme | Origin | Producer |
| --- | --- | --- |
| Subtilisina BPN' | *Bacillus amyloliquefaciens* | SIGMA Chem. Co. St. Louis - USA |
| Subtilisina Carlsberg | *Bacillus subtilis* | SIGMA Chem. Co. St. Louis - USA |
| Alcalase | *Bacillus licheniformis* | NOVO Industri A/S Denmark |

The previously discussed hydrolysis reaction (step (c)) of the R(+) enantiomer of the non-reacted ester (II) is preferably performed under vigorous stirring of a mixture including the non-reacted ester and an aqueous solution of the raw or purified enzyme.

Alternatively, the enzyme may be immobilized on substrates as are known to those skilled in the art.

The enzyme is present in the reaction mixture in an amount from about 0.5% to 30% by weight of the non-reacted ester. The concentration of non-reacted ester II, rich in enantiomer R(+), in the reaction mixture is from about 1% to 20% by weight of the mixture.

According to the present invention, the hydrolysis of step (c) is carried out at a temperature ranging from about 5° C. to 60° C., preferably, from about 10° C. to 40° C. During the reaction, the pH is maintained from about 5 to 10, preferably from about 6 to 9. The pH is controlled by using a buffer, preferably a Na or K buffer solution. Another way of controlling pH is by neutralizing acids formed during the reaction, by addition of a base such as, for example, NaOH, KOH, and LiOH. The hydrolysis of step (c) proceeds for a period from about 5 to 72 hours, depending on the specific activity of the enzyme used.

At the end of the reaction, the resulting mixture, which contains an alkaline salt of 3,4-epoxybutyric acid, predominantly as the R(+) enantiomer, is washed with a solvent immiscible with water such as methylene chloride, toluene, ligroine, ethyl ether, etc., forming aqueous and nonaqueous phases. The alkaline salt of 3,4-epoxybutyric acid is in the aqueous phase.

A molar excess of an aqueous solution of trimethylamine is added to the aqueous phase containing the alkaline salt of 3,4-epoxybutyric acid. Typically, from about 1.5 to 3.0 moles per mole of the alkaline salt of 3,4-epoxybutyric acid (III) of a 0.1 to 5.5 moles/liter solution of trimethylamine is added. The resulting mixture is stirred for between 1 to 12 hours, at a temperature from about 10° to 60° C., preferably between 40° to 50° C.

When the reaction is complete, water and non-reacted trimethylamine are removed by distillation; a residue remains.

NMR analysis of the residue in D$_2$O demonstrates the exclusive presence of L(−)-carnitine as an internal salt, having the formula:

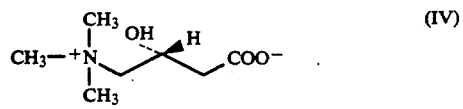

The residue, remaining after removal of the water and trimethylamine, is treated with aqueous hydrochloric acid to obtain an aqueous solution of L(−)-carnitine chloride having formula (I).

The water is evaporated from the aqueous solution leaving a residue which is crystallized in accordance with known techniques, to obtain the desired L(−)-carnitine chloride of formula (I).

The L(−)-carnitine chloride prepared in accordance with the present invention may be used to obtain other derivatives of L(−)-carnitine, such as salts of inorganic acids (HBr, etc.) or organic acids (oxalic acid, etc.)

The following examples are illustrative of the present invention and should not be construed as a limitation thereof.

The following abbreviations are used:

Eu(hfc)$_3$ - europium tris [3-(heptafluoropropylhydroxymethylene)-d-camphorate ].

e.e. - enantiomeric excess.

EXAMPLE 1

Step (a)

The following ingredients were added to 45 ml of a 0.1M KCl solution:

(1) 45 ml of a buffer solution containing Na phosphate at pH=7;

(2) 10 g of isobutyl (R,S)-3,4-epoxybutyrate (63.3 mmoles); and (3) 640 mg of steapsin enzyme (swine pancreas lipase available from SIGMA Chem. Co., USA, having a protein content of 35% and an activity equal to 35–70 units per mg of protein).

The reaction mixture was vigorously stirred for 22 hours at 20° C. During the reaction time, the pH was kept constant at 7 by adding an aqueous solution of 5N NaOH. At the end of the 22 hour reaction period (65% conversion of 3,4-epoxybutyrate), the unreacted ester was recovered from the reaction mixture by extraction with methylene chloride and purified by distillation. 3.3 g of isobutyl R(+) -3,4-epoxybutyrate was recovered. NMR analysis at 300 MHz, in the presence of Eu(hfc)$_3$ (0.05 moles per mole of ester) showed an e.e.≧90%.

Steps (b)+(c)

1 ml of a Na phosphate buffer solution pH 7, 3.3 g of isobutyl R(+)-3,4-epoxybutyrate (20.9 mmoles) obtained from step (a), and 30 mg of the enzyme subtilisina BPN' (available from SIGMA Chem. Co., USA, having an activity of 6 to 9 units per mg of solid), were added to 30 ml of water. The reaction mixture was vigorously stirred for 70 hours at 20° C. The pH was kept constant at 7 throughout the reaction time, by addition of an aqueous solution of 1N NaOH.

After completion of the reaction, the resulting mixture was extracted with methylene chloride resulting in aqueous and organic phases. Then, 5 ml of an aqueous solution of 5N trimethylamine were added to the aqueous phase. The resulting solution was brought to 45° C. and vigorously stirred for two hours.

The solution was then evaporated under reduced pressure (about 20 mm Hg) leaving a residue. A sample of the residue, analyzed by NMR in $D_2O$, was shown to contain the L(−)-carnitine of formula (IV). The residue was dissolved with 3 ml of concentrated aqueous hydrochloric acid. Then, the solution was evaporated under reduced pressure and the remaining residue treated with ethanol. The resulting ethanol solution was boiled for 20 minutes and filtered. On cooling, 3.28 g of L(−)-carnitine chloride, $[\alpha]_D^{20}=21.3°$ (c=1, $H_2O$), e.e.=90%, were crystallized and recovered from the filtrate.

EXAMPLE 2

Step (a)

The reaction mixture was prepared as in Example 1, step (a) except using 10 g of n-butyl (R,S)-3,4-epoxybutyrate (63.3 mmoles). After 26 hours (60% ester conversion), 3.8 g of n-butyl R(+)-3,4-epoxybutyrate were recovered by extraction with methylene chloride and subsequent distillation.

NMR analysis at 300 MHz, in the presence of Eu(hfc)₃, showed an e.e.≧90%.

Steps(b)+(c)

The reaction mixture was prepared as in Example 1, steps (b) and (c) except using the 3.8 g of n-butyl R(+)-3,4-epoxybutyrate (24.1 mmoles) obtained in step (a) hereof. 3.8 g of L(−)-carnitine chloride, $[\alpha]_D^{20}=-22.0°$ C. (c=1, $H_2O$), e.e.≧93%, were obtained.

EXAMPLES 3-8

The processes were performed as in Example 1, except for the changes indicated in Table 1. The yields are also reported in Table 1.

TABLE I

| EXAMPLE No. | R | Step (a) ENZYME (amount) | TIME (hours) | ESTER CONV. % | % e.e. ESTER RESIDUE |
|---|---|---|---|---|---|
| 3 | iso-butyl | Lipase from *Candida Cylindracea* (400 mg) | 39 | 57% | 74% |
| 4 | iso-butyl | Esterase from swine liver (3.5 mg) | 8 | 52% | 62% |
| 5 | iso-butyl | Pancreatin (240 mg) | 21 | 60% | 75% |
| 6 | n-octyl | Steapsin (500 mg) | 24 | 60% | ≧95% |
| 7 | methyl | Lipase from *Candida Cylindracea* (400 mg) | 48 | 60% | 50% |
| 8 | benzyl | Steapsin (500 mg) | 6.5 | 62% | 58% |

| EXAMPLE No. | R | Step (b) ENZYME (amount) | TEMP. | TIME (hours) | g. of CARNITINE CHLORIDE | e.e. % CARNIT. CHLORIDE |
|---|---|---|---|---|---|---|
| 3 | iso-butyl | Subtilisina Carlsberg (50 mg) | 20° | 12 | 4.0 | 75% |
| 4 | iso-butyl | Subtilisina Carlsberg (50 mg) | 20° | 12 | 4.5 | 64% |
| 5 | iso-butyl | Subtilisina BPN' (30 mg) | 20° | 70 | 3.7 | 73% |
| 6 | n-octyl | Alcalase L (400 mg) | 20° | 15 | 2.8 | 95% |
| 7 | methyl | Alcalase L (400 mg) | 20° | 15 | 5.1 | 51% |
| 8 | benzyl | Alcalase T (200 mg) | 40° | 18 | 2.9 | 60% |

EXAMPLE 9

Step (a)

50 ml of nutrient broth (available from Oxoid Ltd., UK) in a 250 ml flask were inoculated with the content of a slant of *Arthrobacter simplex* (IFO 3530) and incubated for 18 hours at 37° C. with stirring at 200 revolutions per minute.

Then, 100 ml of nutrient broth in a 500 ml flask were inoculated with 4 ml of the grown culture and incubated for 12 hours at 37° C. with stirring at 200 revolutions per minute.

Then, 50 ml of a potassium phosphate buffer solution pH7, and 5 g of isobutyl (R,S)-3,4-epoxybutyrate were added to the flask containing the culture, and the resulting reaction mixture was stirred for 48 hours at 20° C.

At the end of the reaction period, the mixture was extracted with methylene chloride. The solvent was then evaporated leaving a residue containing isobutyl 3,4-epoxybutyrate. The residue was purified by chromatography on a silica column. 2.25 g of isobutyl R(+)-3,4-epoxybutyrate having an e.e.=75% was recovered.

Steps (b)+(c)

The processes set forth in steps (b) and (c) of Example 1 were followed. A yield of 2.03 g of L(−)-carnitine chloride having an e.e.=75% was obtained.

EXAMPLE 10

The procedure of Example 9 was followed with the microorganism *Pseudomonas fragi* (IFO 3458).

2.35 g of isobutyl R(+)-3,4-epoxybutyrate having an e.e.=56% was obtained from step (a). From this ester, a yield of 2.12 g of L(−)-carnitine chloride having an e.e.=53% was obtained.

EXAMPLE 11

The procedure of Example 9 was followed with the microorganism *Bacillus subtilis* (ATCC 6633).

2.85 g of isobutyl R(+)-3,4-epoxybutyric acid having an e.e.=52% was obtained from step (a). From this ester a yield of 2.49 g. of L(−)-carnitine chloride having an e.e.=51% was obtained.

EXAMPLE 12

Step (a)

50 ml of a culture medium having the following composition:

0.3% of yeast extract (from Oxoid Ltd. UK);
1% of peptone (from Oxoid Ltd. UK); and
2% glucose was inoculated with the content of a slant of *Rodotorula minuta* (IFO 0879).

The inoculated medium was placed into a 500 ml flask and incubated for 18 hours at 28° C. with stirring at 160 revolutions per minute.

4 ml of the grown culture were drawn and used to inoculate 100 ml of a culture medium having the composition previously described.

0.5 g of calcium carbonate was added and the resulting reaction mixture was maintained at 28° C. with stirring at 160 revolutions per minute.

After 24 hours, 5 g of isobutyl (R,S)-3,4-epoxybutyrate were added to the reaction mixture and maintained at 20° C. for 72 hours, with stirring.

At the end of the reaction time, the mixture was extracted with the solvent methylene chloride. The solvent was then evaporated, leaving a residue containing isobutyl R(+)-3,4-epoxybutyric acid which was purified by chromatography on a silica column.

3.1 g of isobutyl R(+)-3,4-epoxybutyrate having an e.e.=27% was obtained.

Steps (b)+(c)

The procedure set forth in steps (b) and (c) of Example 1 were followed. A yield of 2.8 g of L(−)-carnitine chloride having an e.e.=28% was obtained.

EXAMPLE 13

The procedure of Example 12 was followed with the microorganism *Candida cylindracea* (ATCC 14830).

2.75 g of isobutyl R(+)-3,4-epoxybutyric acid having an e.e.=47% was obtained from step (a). From this ester, a yield of 2.5 g of L(−)-carnitine chloride having an e.e.=45% was obtained.

What is claimed is:

1. A process for preparing L(−)-carnitine chloride, having the formula $$\begin{array}{c} CH_3 \\ | \quad OH \quad H \\ CH_3-{}^+N \diagup\diagdown\diagup\diagdown COOH \quad Cl^- \\ | \\ CH_3 \end{array} \quad (I)$$

comprising the steps of:
(a) reacting a racemic ester of (R,S)-3,4-epoxybutyric acid having the formula $$CH_2-CH-CH_2-COOR \quad (II)$$
$$\diagdown O \diagup$$

wherein R is an alkyl group having from 1 to 10 carbons or a benzyl group, with an enzyme selected from the group consisting of steapsin, pancreatin, esterase from swine liver, and lipase obtainable from *Candida cylindracea*, or with a microorganism producing said enzyme selected from the group consisting of *Pseudomonas fragi* IFO 3458, *Bacillus subtilis* ATCC 6633, *Rodoturula minuta* IFO 0879, *Candida cylindracea* ATCC 14830 and *Arthrobacter simplex* IFO 3530, said enzyme being capable of selectively hydrolyzing enantiomer S(−), asymmetrically, under controlled pH conditions;

(b) separating the hydrolyzed enantiomer S(−) from non-reacted ester (II), which is present as predominantly the R(+) enantiomer;

(c) reacting the non-reacted ester (II) obtained in step (b) with an enzyme capable of quantitatively hydrolyzing the R(+) enantiomer selected from the group consisting of subtilisina BPN', Subtilisina Carlsberg, and ALCALASE, under controlled pH conditions, to thereby obtain a salt of 3,4-epoxybutyric acid, as predominantly the R(+) form having the formula $$CH_2-CH-CH_2-COO^-X^+ \quad (III)$$
$$\diagdown O \diagup$$

wherein X is Na, K, Li;

(d) reacting the R(+) salt of 3,4-epoxybutyric acid obtained in step (c) with a molar excess of trimethylamine; and (e) treating the reaction product of step (d) with HCl to remove the excess trimethylamine and to thereby obtain the L(−)-carnitine chloride of formula (I).

2. The process of claim 1, wherein the hydrolyzing enzymes of steps (a) and (c) are immobilized on a substrate.

3. The process of claim 1, wherein in step (a), the hydrolyzing enzyme is present in an amount of from about 0.03% to 10% by weight of the racemic ester (II).

4. The process of claim 1, wherein in step (a), the asymmetric hydrolysis of the racemic ester is carried out at a temperature of from about 10° C. to 30° C.

5. The process of claim 1, wherein in step (a), the asymmetric hydrolysis of the racemic ester is carried out at a pH of from about 5 to 9.

6. The process of claim 1, wherein the pH is controlled with a basic buffer solution.

7. The process of claim 1, wherein in step (a) the concentration of the racemic ester is from about 1% to 20% by weight of the reaction mixture.

8. The process of claim 1, wherein the enzyme used in step (c) is immobilized on a substrate.

9. The process of claim 1, wherein in step (c) the enzyme is present in an amount of from about 0.5% to 30% by weight of the ester.

10. The process of claim 1, wherein in step (c) the hydrolysis is carried out at a temperature of from about 10° C. to 40° C.

11. The process of claim 1, wherein in step (c) the hydrolysis is carried out at a pH of from about 5 to 10.

12. The process of claim 1, wherein in step (c) the concentration of the ester is from about 1% to 20% by weight of the reaction mixture.

13. The process of claim 1, wherein in step (d) the trimethylamine is added as an aqueous solution in a concentration of from about 0.1 to 5.5 moles/liter, calculated as a molar ratio from about 1.5 to 3 moles per each mole of the salt of R(+)-3,4-epoxybutyric acid (III).

14. The process of claim 13, wherein the temperature is from about 10° C. to 60° C.

15. The process of claim 14, wherein the temperature is from about 40° C. to 50° C.

* * * * *